United States Patent [19]

Welch, Jr.

[11] 4,448,732

[45] May 15, 1984

[54] 2-OXO-1,3-DIOXOL-4-YLMETHYL ESTERS OF PENICILLANIC ACID 1,1-DIOXIDE

[75] Inventor: Willard M. Welch, Jr., Mystic, Conn.

[73] Assignee: Pfizer Inc., New York, N.Y.

[21] Appl. No.: 415,281

[22] Filed: Sep. 7, 1982

[51] Int. Cl.³ .................. C07D 499/00; A61K 31/425
[52] U.S. Cl. .................................. 260/245.2; 424/270;
424/271; 260/239.1
[58] Field of Search .................... 260/245.2 R, 239.1;
424/270, 271

[56] References Cited

U.S. PATENT DOCUMENTS 4,234,579 11/1980 Barth .................................. 424/246
4,359,472 11/1982 Hamanaka .................... 260/245.2 R
4,389,408 6/1983 Sakamoto et al. ........... 260/245.2 R

FOREIGN PATENT DOCUMENTS 39086 11/1981 European Pat. Off. .

Primary Examiner—Nicholas S. Rizzo
Attorney, Agent, or Firm—Charles J. Knuth; Albert E. Frost; J. Trevor Lumb

[57] ABSTRACT

Certain novel 2-oxo-1,3-dioxol-4-ylmethyl esters of penicillanic acid 1,1-dioxide (sulbactam) hydrolyze readily in vivo to liberate the corresponding free acid. The novel esters of this invention are useful therefore as antibacterial agents and beta-lactamase inhibitors.

5 Claims, No Drawings

2-OXO-1,3-DIOXOL-4-YLMETHYL ESTERS OF PENICILLANIC ACID 1,1-DIOXIDE

BACKGROUND OF THE INVENTION

This invention relates to new chemical compounds, which are of value as antibacterial agents and beta-lactamase inhibitors. More particularly this invention provides certain 2-oxo-1,3-dioxol-4-ylmethyl esters of penicillanic acid 1,1-dioxide (sulbactam).

U.S. Pat. No. 4,234,579 discloses penicillanic acid 1,1-dioxide, and certain esters thereof readily hydrolyzable in vivo, as antibacterial agents and beta-lactamase inhibitors. In particular, U.S. Pat. No. 4,234,579 discloses esters of the formula

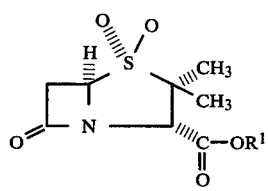
(I)

wherein $R^1$ is 3-phthalidyl, 4-crotonolactonyl, gamma-butyrolacton-4-yl or a group of the formula

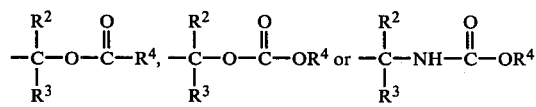

wherein $R^2$ and $R^3$ are each hydrogen, methyl or ethyl and $R^4$ is alkyl of 1 to 6 carbons. Said esters of formula I are readily cleaved in vivo to liberate penicillanic acid 1,1-dioxide.

However, it is an object of this invention to provide a new genus of esters of penicillanic acid 1,1-dioxide which hydrolyze readily in vivo to liberate penicillanic acid 1,1-dioxide. Specifically these new esters of penicillanic acid 1,1-dioxide are certain 2-oxo-1,3-dioxol-4-ylmethyl esters.

Certain 2-oxo-1,3-dioxol-4-ylmethyl esters of ampicillin are disclosed in published European patent application No. 39,086.

SUMMARY OF THE INVENTION

This invention provides novel esters of penicillanic acid 1,1-dioxide of the formula

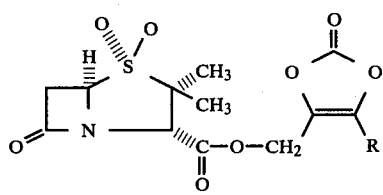
(II)

wherein R is selected from the group consisting of hydrogen, methyl and phenyl.

Said compounds of formula II readily hydrolyze to penicillanic acid 1,1-dioxide in vivo, and therefore they are useful as antibacterial agents and beta-lactamase inhibitors.

DETAILED DESCRIPTION OF THE INVENTION

This invention relates to the novel compounds of formula II, and throughout this specification they are referred to as derivatives of penicillanic acid, which is represented by the structural formula

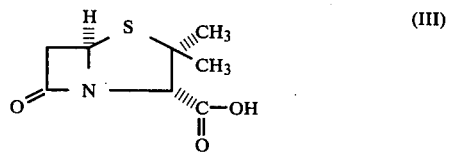
(III)

In formula III, broken line attachment of a substituent to the bicyclic nucleus indicates that the substituent is below the plane of the bicyclic nucleus. Such a substituent is said to be in the alpha-configuration. Conversely, solid line attachment of a substituent to the bicyclic nucleus indicates that the substituent is attached above the plane of the nucleus. This latter configuration is referred to as the beta-configuration.

Also, in this specification, certain compounds are named as derivatives of 4-methyl-2-oxo-1,3-dioxole, the compound of formula IV. Moreover, the term 2-oxo-1,3-dioxol-4-ylmethyl is used for the radical of formula V.

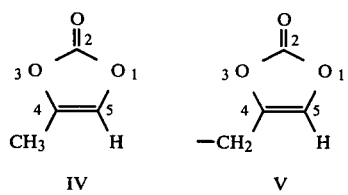

The compound of formula IV is named 4-methyl-1,3-dioxolen-2-one, and the radical V is named (2-oxo-1,3-dioxolen-4-yl)methyl, in published European patent application No. 39,086.

The compounds of formula II can be prepared directly from penicillanic acid 1,1-dioxide by esterification. Thus the compounds of formula II can be prepared by reacting a compound of the formula

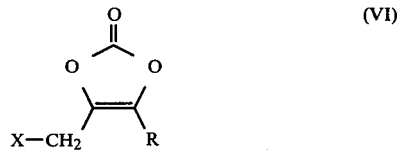
(VI)

with a carboxylate salt of penicillanic acid 1,1-dioxide of the formula

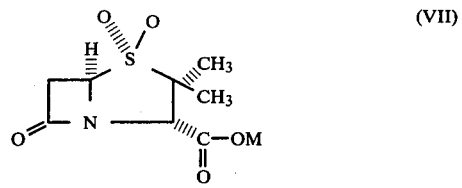
(VII)

wherein R is hydrogen, methyl or phenyl, X is a good leaving group, and M is a carboxylate salt forming cation. Useful leaving groups for X are halogen atoms, such as chloro, bromo and iodo, and useful carboxylate salts for compound VII are alkali metal salts, such as sodium and potassium salts, amine salts, such as triethylamine salts, and tetraalkylammonium salts, such as tetra-n-butylammonium salts.

The reaction between a compound of the formula VI and a compound of formula VII is usually carried out by contacting the reagents in an organic solvent, at a temperature in the range from 0° to 80° C., and preferably from 30° to 60° C. The compounds of formulae VI and VII are normally contacted in equimolar proportions, but an excess of either compound can be used. A wide variety of solvents can be used, and typical solvents are low-molecular weight ketones, such as acetone and methyl ethyl ketone, N,N-dimethylformamide, N,N-dimethylacetamide, N-methylpyrrolidone and hexamethylphosphoramide. The reaction time varies according to a number of factors, but at about 55° C. reaction times of a few hours, e.g. 12 to 24 hours are commonly used.

The compound of formula II can be isolated by conventional methods. For example, the reaction mixture can be filtered and then the solvent removed by evaporation in vacuo. The residue is then partitioned between water and a water-immiscible, volatile, organic solvent, such as ethyl acetate. The ethyl acetate layer is dried and evaporated to afford the compound of formula II.

The compounds of formula II can be purified by conventional methods, such as recrystallization and/or chromatography.

The compounds of formula VI can be prepared by the methods described in published European patent application No. 39,086.

As indicated hereinbefore, the compounds of formula II are readily hydrolyzed in vivo to liberate penicillanic acid 1,1-dioxide, and therefore they can be used for the same purposes as the esters of penicillanic acid 1,1-dioxide readily hydrolyzable in vivo disclosed in U.S. Pat. No. 4,234,579. In particular, the compounds of formula II are formulated in the same way, they are administered by the same methods and routes to the same hosts, and they are administered at the same dosages as the esters of penicillanic acid 1,1-dioxide readily hydrolyzable in vivo disclosed in U.S. Pat. No. 4,234,579.

The following Examples and Preparations are provided solely for further illustration. Nuclear magnetic resonance (NMR) spectra were measured at 60 MHz. The following abbreviations for peak shapes are used: s, singlet; d, doublet; t, triplet.

EXAMPLE 1

5-Methyl-2-oxo-1,3-dioxol-4-ylmethyl Penicillanate 1,1-Dioxide

To a stirred suspension of 3.07 g of sodium penicillanate 1,1-dioxide and 2.33 g of 4-bromomethyl-5-methyl-2-oxo-1,3-dioxole in 100 ml of acetone was added 200-300 mg of tetra-n-butylammonium bromide, and then the reaction mixture was heated under reflux overnight. The reaction mixture was filtered hot, and the resulting solution was evaporated in vacuo. The residue was dissolved in ethyl acetate and the resulting solution was washed with dilute aqueous sodium chloride solution. The ethyl acetate solution was dried and evaporated in vacuo, and then the residue was chromatographed on silica gel using 1:1 hexane-ethyl acetate. The product-containing fractions were combined and evaporated in vacuo, and the residue was recrystallized from ethyl acetate-petroleum ether to give 2.80 g of the title product as a crystalline solid, m.p. 141.5°–2.5° C.

The NMR spectrum of the product (CDCl$_3$) showed absorptions at 1.55 (3H, s), 1.63 (3H, s), 2.20 (3H, s), 3.46 (2H, d, J=3 Hz), 4.40 (1H, s), 4.45 (1H, t, J=3 Hz) and 4.97 (2H, s) ppm downfield from tetramethylsilane. The infrared spectrum (KBr disc) showed absorptions at 5.46, 5.58 and 5.67 microns. The mass spectrum showed peaks at m/e 345, 280, 239, 212, 168, 111 and 83 (100%).

Analysis: Calcd. for C$_{13}$H$_{15}$O$_8$NS: C, 45.21; H, 4.38; N, 4.06. Found: C, 45,36; H, 4.49; N, 4.03.

EXAMPLE 2

By repeating the procedure of Example 1, but replacing the 4-bromomethyl-5-methyl-2-oxo-1,3-dioxole by an equimolar amount of 4-bromomethyl-2-oxo-1,3-dioxole and 4-bromomethyl-5-phenyl-2-oxo-1,3-dioxole, respectively, the following compounds can be prepared:

2-oxo-1,3-dioxol-4-ylmethyl penicillanate 1,1-dioxide and 5-phenyl-2-oxo-1,3-dioxol-4-ylmethyl penicillanate 1,1-dioxide, respectively.

PREPARATION 1

4-Bromomethyl-5-methyl-2-oxo-1,3-dioxole

To a stirred solution of 3.0 g of 4,5-dimethyl-2-oxo-1,3-dioxole in 100 ml of carbon tetrachloride was added 4.63 g of N-bromosuccinimide. The resulting solution was heated under reflux and irradiated for 15 minutes. The reaction mixture was cooled to 0°–5° C., filtered and evaporated to give the title product.

The NMR spectrum (CDCl$_3$) showed absorptions at 2.05 (5% of starting material), 2.18 (3H, s), 4.30 (2H, s) and 4.35 (5% of dibromo compound) ppm downfield from tetramethylsilane. The infrared spectrum showed an absorption at 5.49 microns.

PREPARATION 2

4,5-Dimethyl-2-oxo-1,3-dioxole

A solution of phosgene (12.18 g) in cold dichloromethane was added dropwise to a cold solution of 3-hydroxy-2-butanone (10.83 g) and 16.38 g of N,N-dimethylaniline in 50 ml dichloromethane. The resulting green solution was stirred 2 hours at 0°–5° C. The solution was then evaporated to give an oil which was heated at 160°–190° C. for 30 minutes. The cooled reaction mixture was partitioned between water and ether. The separated aqueous layer was further extracted with ether and the combined organic extracts were dried and concentrated. The residue was triturated with pentane to give 3.53 g (25%) of a white crystalline solid, m.p. 76°–78° C.

The NMR spectrum of the product (CDCl$_3$) showed an absorption at 2.05 (s) ppm downfield from tetramethylsilane. The mass spectrum showed peaks at m/e 114, 56 and 43 (100%).

I claim:

1. A compound of the formula

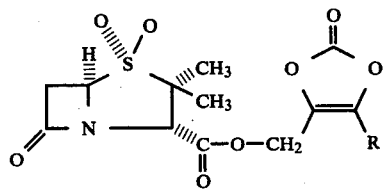
wherein R is selected from the group consisting of hydrogen, methyl and phenyl.
2. The compound according to claim 1, wherein R is hydrogen.
3. The compound according to claim 1, wherein R is methyl.
4. The compound according to claim 3, when in crystalline form.
5. The compound according to claim 1, wherein R is phenyl.
* * * * *